(12) United States Patent
Betancourt et al.

(10) Patent No.: US 7,081,615 B2
(45) Date of Patent: Jul. 25, 2006

(54) METHODS AND APPARATUS FOR THE DOWNHOLE CHARACTERIZATION OF FORMATION FLUIDS

(75) Inventors: Soraya S. Betancourt, Ridgefield, CT (US); Anthony Goodwin, Cambridge (GB); Go Fujisawa, Danbury, CT (US); Oliver C. Mullins, Ridgefield, CT (US); Hani Elshahawi, Houston, TX (US); Julian Pop, Houston, TX (US); Terizhandur S. Ramakrishnan, Bethel, CT (US); Li Jiang, Cambridge (GB)

(73) Assignee: Schlumberger Technology Corporation, Ridgefield, CT (US)

( * ) Notice: Subject to any disclaimer, the term of this patent is extended or adjusted under 35 U.S.C. 154(b) by 254 days.

(21) Appl. No.: 10/309,849

(22) Filed: Dec. 3, 2002

(65) Prior Publication Data

US 2004/0104341 A1 Jun. 3, 2004

(51) Int. Cl.
*G01N 9/00* (2006.01)
(52) U.S. Cl. .................................................. 250/255
(58) Field of Classification Search ................ 250/255
See application file for complete search history.

(56) References Cited

U.S. PATENT DOCUMENTS

| | | | |
|---|---|---|---|
| 4,994,671 A | 2/1991 | Safinya et al. ............... | 250/255 |
| 5,622,223 A * | 4/1997 | Vasquez ..................... | 166/264 |
| 5,780,850 A * | 7/1998 | DeLaune et al. ............ | 250/255 |
| 5,939,717 A | 8/1999 | Mullins ....................... | 250/255 |
| 6,274,865 B1 | 8/2001 | Schroer et al. ........... | 250/269.1 |
| 6,683,681 B1 * | 1/2004 | DiFoggio et al. ............ | 356/128 |
| 2002/0043620 A1 | 4/2002 | Tchakarov et al. ....... | 250/269.1 |

FOREIGN PATENT DOCUMENTS

| | | | |
|---|---|---|---|
| GB | 2 304 906 | | 3/1997 |
| GB | 2345137 A | * | 6/2000 |
| WO | WO 98/45575 | | 10/1998 |

OTHER PUBLICATIONS

Craft, B. C. et al. "Applied Petroleum Reservoir Engineering", *Prentice Hall*, pp. 59-67, (1959).
Ely, J. F. et al. "Prediction of Transport Properties. 1. Viscosity of Fluids and Mixtures". *I & EC Fund.*, vol. 20, No. 4, pp. 323-332, pp. 323-332, (1981).

(Continued)

*Primary Examiner*—David Porta
*Assistant Examiner*—Shun Lee
(74) *Attorney, Agent, or Firm*—Jody Lynn DeStefanis; William L. Wang; David P. Gordon

(57) ABSTRACT

Methods and apparatus for investigating a hydrocarbon bearing geological formation traversed by a borehole are disclosed. A borehole tool is used to acquire a sample of fluid in the formation. Compositional analysis of the fluid sample is conducted to provide a determination of the composition of the sample. The sample composition is then related to a model of the thermodynamic behavior of the fluid; i.e., the mass fractions of the fluid components are used as inputs to an equation of state (EOS) to predict the phase behavior of the fluid.

8 Claims, 13 Drawing Sheets

OTHER PUBLICATIONS

Lake, L. W. "Enhanced Oil Recovery". *Prentice Hall*, Chap. 4, pp. 93-104, (1999).

Michelsen, J. L. Calculation of Phase Envelopes and Cirtical Points for Multicomponent Mixtures:. *Fluid Phase Equilibria*, vol. 4, pp. 1-10, (1980).

Pedersen, K. S. et al. "Properties of Oils and Natural Gases". *Gulf Publishing Co.*, Chap. 5 pp. 79-88, Chap. 11 pp. 172-175, (1989).

Firoozabadi, Abbas Thermodynamics of Hydrocarbon Reservoirs. Chapter 3 Equation-of-State Representation of Reservoir-Fluids Phase Behavior and Properties. *McGraw-Hill Companies, Inc.* (1999) pp. 129-153.

McCain, Jr., William D. The Properties of Petroleum Fluids. Chapter 5 The Five Reservoir Fluids. *Penwell Publishing Co.* (1990) pp. 147-159.

Schlumberger. PVTi Reference Manual 2002A. Chapter 7 Technical Description. *Schlumberger Information Solutions* (Jul. 2002) pp. 7-1 to 7-17, pp. 7-26 to 7-43, and pp. 7-46 to 7-54.

* cited by examiner

US 7,081,615 B2

METHODS AND APPARATUS FOR THE DOWNHOLE CHARACTERIZATION OF FORMATION FLUIDS

This application is related to co-owned U.S. Pat. No. 5,859,430 to O. Mullins et al., entitled "Method and Apparatus for the Downhole Compositional Analysis of Formation Gases", which is hereby incorporated by reference herein in its entirety.

BACKGROUND OF THE INVENTION

1. Field of the Invention

The present invention relates to methods and apparatus for making in situ determinations regarding hydrocarbon bearing geological formations. The present invention more particularly relates to methods and apparatus for conducting phase calculations on samples of downhole fluids. The phase calculations may then be used in order to determine the proximity of the parameters of the formation to one or more of a vapor pressure line, a bubble point curve, a dew point curve, and a critical point for the fluid. The invention has application to downhole testing procedures and to production parameters and procedures, although it is not limited thereto.

2. State of the Art

Characterizing commercially viable accumulations of hydrocarbons is the main objective of well logging. Downhole sampling and testing tools such as the Modular Dynamic Formation Tester (MDT) (MDT being a trademark of Schlumberger Ltd.) are used during the logging phase to gain a more direct assessment of the production characteristics of the accumulation. The objective of the MDT tool is to provide a controlled channel of hydraulic communication between the reservoir fluid and the wellbore. The tool allows withdrawal of small amounts of formation fluid through a probe that contacts the reservoir rock (formation). In addition to obtaining a more direct measurement of the flow characteristics of the reservoir and the formation pressure, high quality samples of fluid can be obtained for analysis. Historically, the fluid samples were brought to the surface for analysis in the laboratory, but recent developments in the MDT tool have made possible the direct measurement of fluid properties downhole during the pump-out or sampling sequence. Details of the MDT tool and the Optical Fluid Analyzer (OFA) module of the MDT tool may be obtained with reference to commonly owned U.S. Pat. No. 3,859,851 to Urbanosky, U.S. Pat. No. 4,994,671 to Safinya et al., U.S. Pat. No. 5,167,149 to Mullins et al., U.S. Pat. No. 5,201,220 to Mullins et al., U.S. Pat. No. 5,266,800 to Mullins et al., and U.S. Pat. No. 5,331,156 to Hines et al., all of which are hereby incorporated by reference in their entireties herein.

The main advantage of downhole analysis is that the fluid is relatively pristine. If the sampling pressure is above the saturation pressure, the fluid will be in a single phase ensuring that the original composition is being analyzed. For pressures below the saturation pressure a measurement of the properties of the liquid phase in the oil zone and the associated gas above it will yield a more accurate sampling than a sample recombined in surface. Indeed, it may be difficult to retain the sample in the state in which it existed downhole when it is retrieved to surface.

Petroleum oil and gas are essentially a mixture of several hydrocarbon components whose variation dictates the characteristics of the fluid. Different types of reservoir fluids include black oils, volatile oils, retrograde condensates, wet gases, and dry gases, and the fluid types require different considerations for their exploitation, and different properties are used for their description. For example, it is generally agreed that black oils and dry gases can be described satisfactorily using averaged properties of the oil and gas phases, such as the volumetric factors and gas solubility ratios. Volatile oils, retrograde condensates and wet gases require a more detailed knowledge of the fluid composition since the ultimate recovery will be dictated by the control of the production conditions (mostly pressure).

A downhole fluid analysis provides information in real time in contrast to a laboratory analysis that may last for several days, or surface wellsite analysis, which may result in undesirable phase transitions as well as the loss of key constituents. One component that can be analyzed downhole is hydrogen sulfide ($H_2S$). Although this component does not significantly affect the phase behavior of the reservoir fluids it is significant for metallurgy of the production string.

A detailed description of the fluid properties is desirable for an accurate modeling of the fluids in the reservoir. Indeed, decisions such as the type of well completion, production procedures and the design of the surface handling and processing facilities are affected by the characteristics of the produced fluids. For example, if fluid in the reservoir is a retrograde condensate, the saturation (dew) pressure, combined with the formation pressure and permeability will dictate the maximum pressure drawdown for production of the fluids, or whether an injection scheme for pressure maintenance or liquid vaporization should be implemented.

SUMMARY OF THE INVENTION

It is therefore an object of the invention to provide apparatus and methods for modeling in situ certain properties of fluids in a reservoir.

It is another object of the invention to provide apparatus and methods for analyzing reservoir fluids in relation to the thermodynamic behavior of the fluids in the formation.

It is a further object of the invention to provide downhole apparatus and methods for using a compositional analysis of fluid obtained from a formation and the thermodynamic behavior of the fluid in the formation in order to make determinations regarding fluid sampling, well completion, or production procedures.

In accord with the objects of the invention, in situ determinations regarding hydrocarbon bearing geological formations are made via the use of a sampling tool such as the Schlumberger Modular Dynamic Formation Tester (MDT). Downhole data acquired with the sampling tool are used to conduct a compositional analysis of the reservoir fluid and the compositional analysis of the reservoir fluid is related to a model of the thermodynamic behavior of the fluid; i.e., the mass fractions of the fluid components are used as inputs to an equation of state (EOS) to predict the phase behavior of the fluid. With the reservoir fluid characterized with respect to its thermodynamic behavior, fluid production parameters, transport properties, and commercially useful indicators of the reservoir are computed. For example, the thermodynamic model can provide the phase envelope that can be used to interactively vary the rate at which samples are collected in order to avoid entering the two-phase region. Other properties that may also be useful in assessing the methods required to produce the particular reserve can be estimated from the chosen equation of state. As examples, the density, viscosity, and volume of gas formed from a liquid after expansion to a specified temperature and pressure may be obtained directly from the EOS or from correlations between EOS calculated properties and composition.

According to another aspect of the invention, the characterization of the fluid sample with respect to its thermodynamic model can be used as a benchmark to determine the validity of the obtained sample, whether to retain the sample, and/or whether to obtain another sample at the location of interest. More particularly, based on the thermodynamic model and information regarding formation pressures, sampling pressures, and formation temperatures, if it determined that the fluid sample was obtained near or below the bubble line of the sample, a decision may be made to jettison the sample and/or to obtain sample at a slower rate (i.e., a smaller pressure drop) so that gas will not evolve out of the sample. Alternatively, because knowledge of the exact dew point of a retrograde gas condensate in a formation is desirable, a decision may be made, when conditions allow to vary the pressure drawdown in an attempt to observe the liquid condensation and thus establish the actual saturation pressure.

In order to generate a relatively accurate thermodynamic model of the reservoir fluid it is desirable to obtain an accurate determination of the reservoir fluid composition. Thus, in accord with a presently preferred embodiment of the invention, the reservoir fluid composition is estimated by the Condensate and Gas Analyzer (CGA) module of the MDT tool. The CGA module measures absorption spectra and translates them into concentrations of several molecular groups in the fluids of interest. In particular, determinations of the concentrations of methane ($CH_4$), a group containing ethane, propane, butane, and pentane fractions ($C_2H_6$, $C_3H_8$, $i-C_4H_{10}$, $n-C_4H_{10}$, $i-C_5H_{12}$, $n-C_5H_{12}$), a lump of hexane and heavier components ($C_6H_{14}+$), and carbon dioxide ($CO_2$), can be calculated. However, the present invention is generalized to any given partitioning of the fluid composition. Thus, if desired, each component of the fluid may be considered separately in order to provide more accuracy in the modeling.

Additional objects and advantages of the invention will become apparent to those skilled in the art upon reference to the detailed description taken in conjunction with the provided figures.

DETAILED DESCRIPTION OF THE PREFERRED EMBODIMENTS

Matter can exist in three basic phases, namely: gas, liquid and solid. The phase behavior of a substance refers to all possible states or phases in which this substance is present under certain conditions of pressure and temperature. A "substance" is formed by one or more identifiable "components" or "chemical entities". The term "system" will also be used in this context as a synonym of "substance".

Gibbs phase rule states that the degrees of freedom of a system ($N_F$), is equal to the number of components ($N_C$) minus the number of phases ($N_P$) plus 2, assuming that there are no chemical reactions among components. The number 2 refers to the intensive properties: pressure and temperature. The degrees of freedom of a system establish the number of independent intensive properties that must be specified to obtain the thermodynamic state of all the properties of the system.

Figure 1:
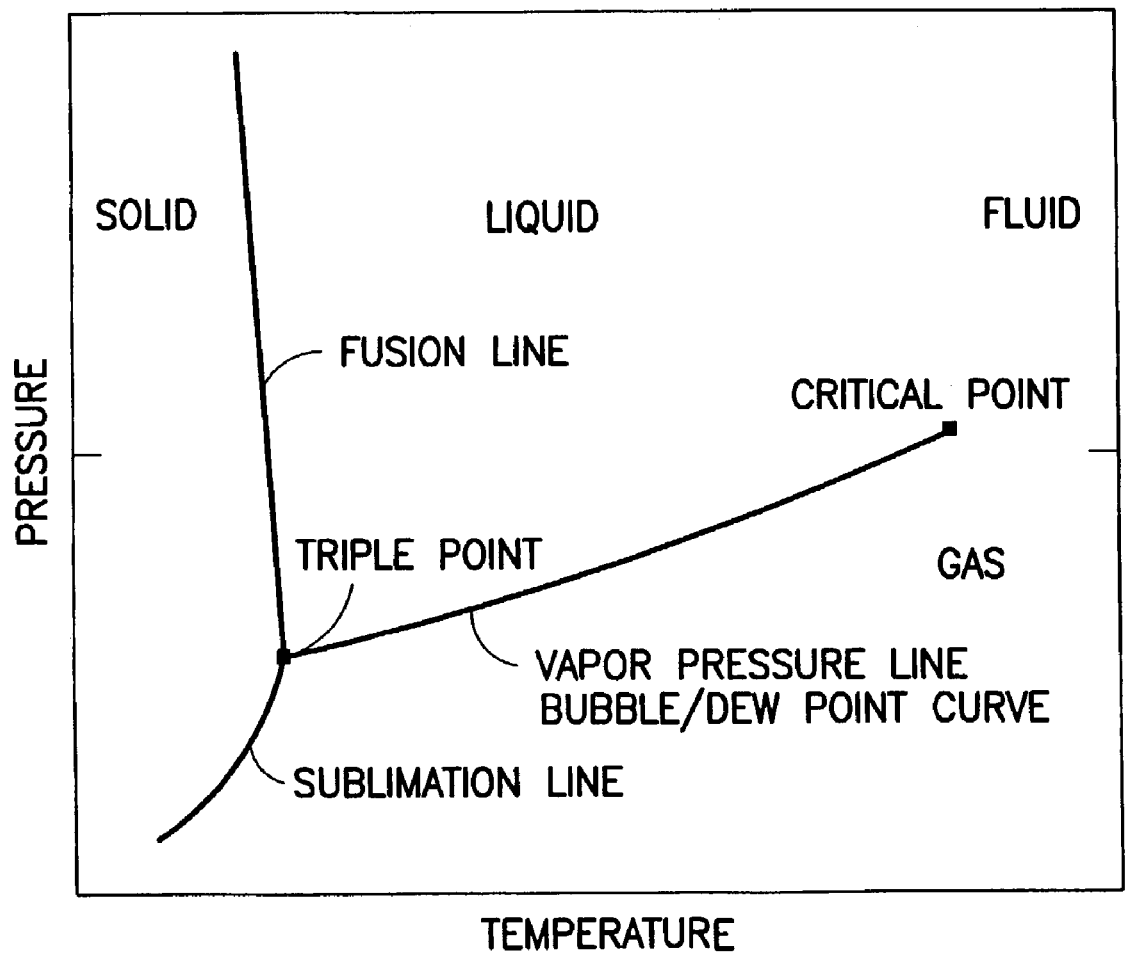
FIG. 1 is a pressure-temperature diagram for a pure component.

FIG. 1 depicts a pressure-temperature (P-T) diagram for a pure component ($N_C=1$). When two phases coexist $N_F$ equals 1 and the two phases are present along any of the lines depicted in FIG. 1. For three phases $N_F=0$, and the three phases can only exist under a certain pressure and temperature specified by the Triple point. A critical point exists at the end of the gas/liquid phase boundary line and this vapor pressure curve has high relevance for the petroleum industry. At the critical point the gas and liquid properties are identical and beyond it the phase transitions occur without discontinuous changes in the fluid properties. In the region with pressure and temperature higher than the critical point, the fluid is called supercritical.

Figure 2:
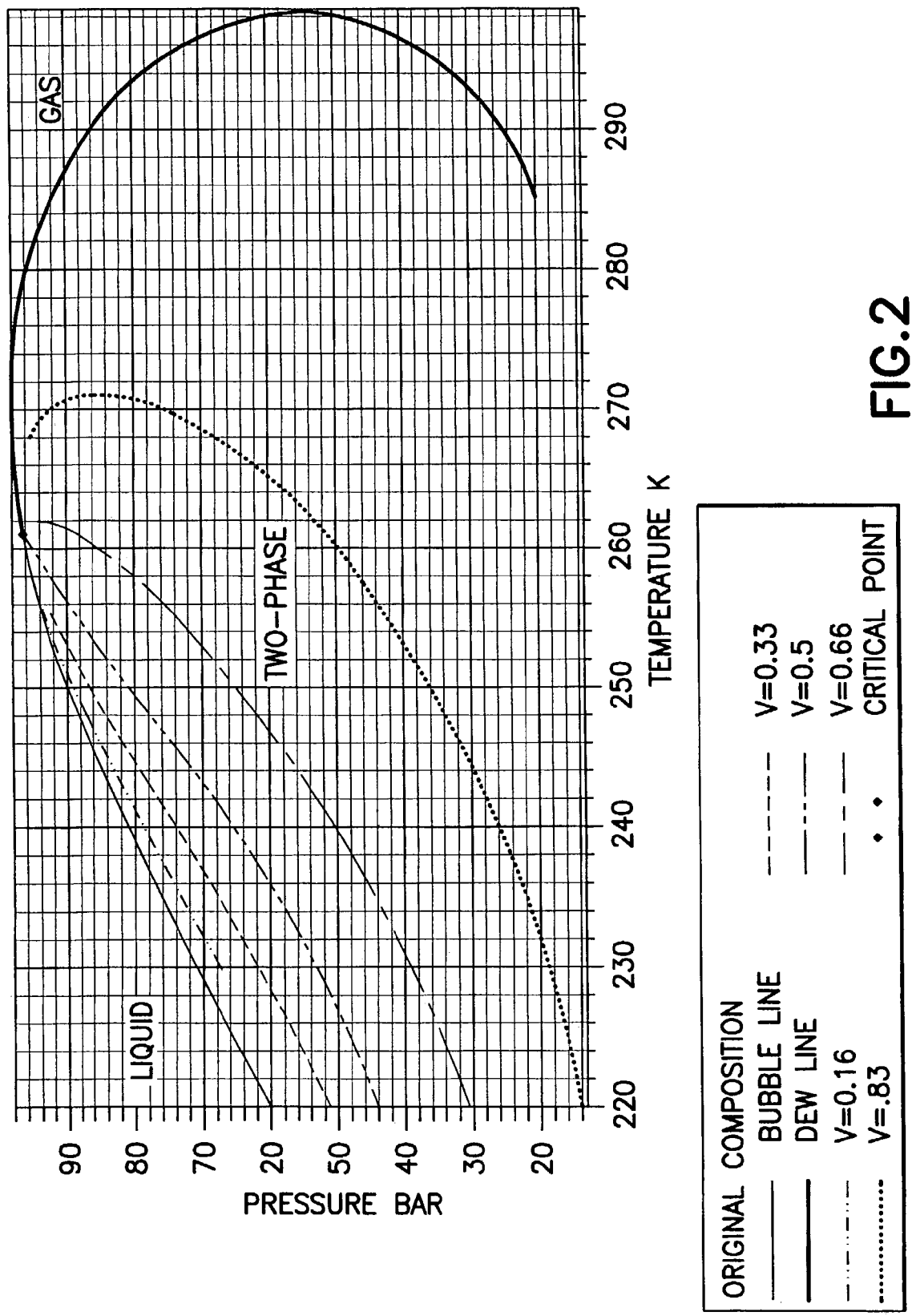
FIG. 2 is a pressure-temperature diagram for a hydrocarbon mixture which shows a bubble line, dew line and critical point for the mixture.

Petroleum fluids (oil and gas) are mixtures of multiple hydrocarbon components ($N_C>2$) with a complicated phase behavior. When two phases are present, $N_F>2$, and the pressure and temperature conditions under which the two phases exist is represented by an area enclosed by an envelope in a P-T diagram. FIG. 2 shows the P-T phase diagram for a hydrocarbon fluid with composition listed in Table 1.

TABLE 1

| Component | Mole Fraction |
|---|---|
| C1 | 0.7102 |
| C2 | 0.1574 |
| C3 | 0.0751 |
| i-C4 | 0.0089 |
| n-C4 | 0.0194 |
| i-C5 | 0.0034 |
| n-C5 | 0.0027 |
| C6 | 0.0027 |
| C7+ ($\gamma = 0.7$, M = 103) | 0.0003 |
| CO2 | 0.0167 |
| N2 | 0.0032 |

In FIG. 1, the bubble and dew curves of the pure component coincide. In the case of a mixture, such as the one presented in FIG. 2, the two curves enclose the two-phase region and meet at the critical point. The lines within the envelope correspond to different mole fractions of vapor (V), and subsequently the bubble line corresponds to V=0 and the dew curve has V=1. It is important to note that the fluid composition is constant in FIG. 2.

As is seen in FIG. 2, the left-most line represents the bubble curve of the mixture. For pressure and temperature conditions above the bubble curve, the fluid is in the liquid phase. If pressure is decreased at a constant temperature below the critical temperature (Tc) (i.e., the temperature at the critical point which marks the delineation between the bubble line and the dew line), the "first" gas bubble will form at the bubble point pressure. In FIG. 2, the right-most line is called the dew curve. Pressure and temperature conditions beyond the dew curve correspond to a single gaseous phase.

The phase envelope is characterized by three properties: the cricondenbar, the cricondentherm and the critical point. The cricondenbar is the point of highest pressure at which the two phases exist (in FIG. 2 this is approximately 98 bar); the cricondentherm is the point of highest temperature at which the two phases are present (in FIG. 2 this is approximately 298° K.); and the critical point is the point where the dew line and the bubble line meet and the fluid phases coalesce. In the vicinity of the critical point the classical equations of state (EOS) cannot provide accurate (within a few degrees K of critical temperature) predictions of the thermodynamic properties of a fluid without recourse to a cross-over model. The critical point of this mixture is shown in FIG. 2 at 96 bar and 260° K.

Equations of state describe mathematically the phase behavior of a fluid by relating three intensive properties of matter: pressure, temperature, and molar volume. In its most basic form the EOS is the ideal gas equation:

$$P = \frac{RT}{V_M} \quad (1)$$

Most EOS used in the oil industry are derivatives of van der Waals equation. These cubic equations were developed to deal with phase equilibria of complex multicomponent mixtures. Their general form is:

$$P = RT/[V_M - b_1(T)] - a(T)/[(V_M + b_2(T))V_M + b_3(T))] \quad (2)$$

where $V_M$ is the molar volume, T is the temperature, and R is the gas constant. The first term in the right side of Equation 2 represents the correction to the molar volume due to the volume occupied by the molecules. The second term represents the contribution to the pressure due to the attraction of the molecules as a function of temperature.

The major failing of the cubic equations of state is that the equations provide only rough predictions of liquid density (i.e., the predictions may be in error by at least 10%). However, a simple empirical correction, known as the volume translation, has been devised that improves this without affecting the phase equilibria predictions. This correction is usually determined by adjusting a coefficient to measured densities. There are other, more complex, equations of state such as the well-known Benedict-Webb-Rubin equations. These equations can require significant processing power depending on the complexity of the fluid and flow-sheet problem. Thus in most oilfield applications the cubic EOS are used. For purposes of the present invention, either the cubic EOS or the more complex EOS may be utilized.

Methods of determining the dew and bubble curves with equations of state are well documented; See, e.g., Michelsen, M. L., "Calculation of Phase Envelopes and Critical Points for Multicomponent Mixtures", *Fluid Phase Equilibria*, 4, 1980 (pp. 1–10) which is hereby incorporated by reference herein in its entirety. Use of the cubic equation of state to determine the dew and bubble curves requires knowledge of the critical temperature, critical pressure, and acentric factor ($\omega$) for each of the components, along with the binary interaction parameters ($b_{ij}$) (which may be set to zero if unknown and may result in a reduction in accuracy of the prediction). The algorithm required to determine the bubble point (which is essentially identical with that required for the dew point) with an equation of state for both phases has been documented in the literature; See, e.g., Michelsen, M. L. id. Essentially, this requires that the composition of the liquid and either the pressure or temperature be fixed and then for an assumed temperature and gas mole fraction the fugacity is calculated with the EOS model. These values are then used to calculate the equilibrium ratio. The process is iterated until the sum of the gaseous mole fractions is equal to unity.

For the case when some fluid components are grouped, schemes can be used to split a grouped composition into individual components at a mole fraction. These procedures, which have been documented in the literature, may increase the accuracy of the predictions from a particular equation of state.

Certain parameters of the selected EOS also may be tuned to additional physical measurements or prior knowledge to obtain a more representative model. If for example, a measurement of the bubble point pressure of a sample is available, the information is incorporated to fit the selected equation of state at this point. Model parameters that can be tuned are the critical pressure, critical temperature, and acentric factor ($\omega$) of each component, the binary interaction coefficients ($b_{ij}$), or the molar composition of the mixture. For cubic EOS, which poorly represents the density of liquids, a measurement of density is desirable to determine the volume correction factor, and thus permit prediction densities with an uncertainty of better than 10%.

Uncertainty in phase calculations is associated with the error involved by the use of an EOS to model the fluid behavior, the uncertainty in the composition of the fluid measured with the downhole tool, and the use of pseudocomponents to represent groups of hydrocarbon fractions. Therefore, according to the preferred embodiment of the invention, the calculations are made in a probabilistic framework and an estimate of the uncertainty in the calculated phase behavior is preferably reported with the result. As a result, process decisions may be made in real-time by computerized systems or operators.

In the special case that the composition and other physical property measurements obtained with the MDT tool correspond to conditions near to critical, the uncertainty in the fluid properties calculated with a cubic equation of state are necessarily higher. However, the information that the fluid is near critical is already of great value. In particular, determining which side of the critical point (that is whether the fluid is a near critical liquid or near critical gas) is extremely useful data for exploration and production decisions. For example, a near critical gas may show retrograde behavior in the production tubulars while a near critical liquid will have a bubble pressure.

In order to demonstrate the performance of the proposed analysis scheme, the composition listed in Table 1 for which the phase boundary is shown in FIG. 2 was taken as a starting point. The components of Table 1 were then grouped according to the groups that are available from the MDT CGA analysis. Thus two groups were formed to represent the fractions C2 to C5 and C6+; i.e., the mole fractions of the components C2 through C5 were combined, and the mole fractions of C6 and larger carbon chains were combined. The phase equilibrium calculations were repeated with this CGA pseudo-composition and the P-T section that resulted is shown in FIG. 3.

Figure 3:
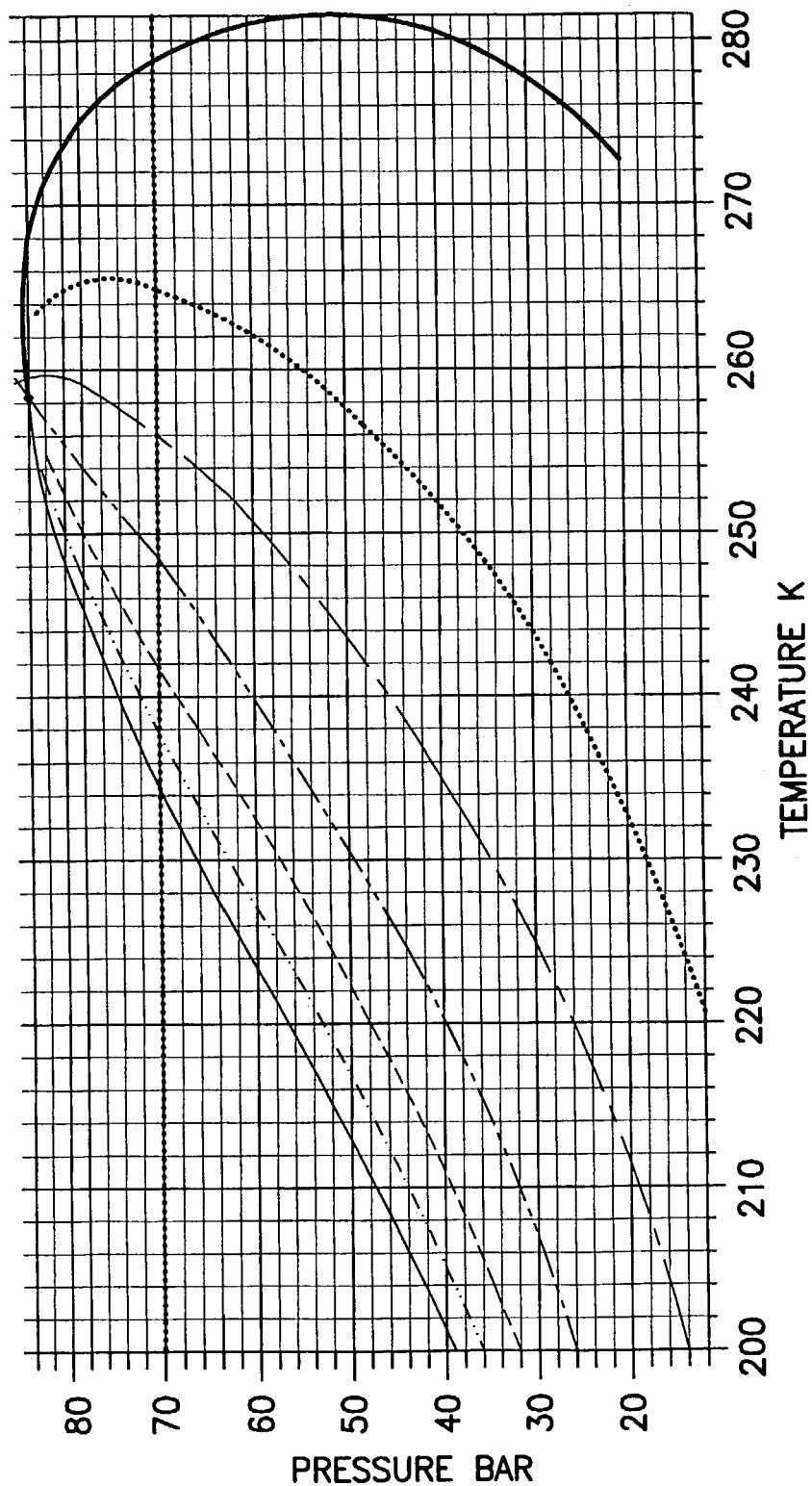
FIG. 3 is a pressure-temperature diagram for a pseudo-composition of hydrocarbons.

For the new pseudo-composition it is seen in FIG. 3 that the cricondenbar is at approximately 87 bar, the cricondentherm is at approximately 282° K. and the critical point is at approximately 86 bar and approximately 258° K. These calculated values are, in general, a little lower than those shown in FIG. 2 for the extended composition listed in table 1. When comparing the values obtained with the pseudo-component analysis with the values determined for the extended composition, the pseudo-component cricondenbar is about 12% lower, the cricondentherm about 5% lower and the critical pressure about 11% lower, while the critical temperature is essentially invariant (i.e., within about 1%). Although this comparison has been performed for only one, albeit typical, fluid the results indicate that the maximum pressure and temperature of the phase diagram estimated with the pseudo-composition can be useful in defining (along with an estimated error) the maximum pressure and temperature drops that the fluid can withstand and still be single phase. Perhaps more notable is the very small variation in predicted critical temperature. This implies that the CGA pseudo-component analysis can be used to distinguish the fluid type of either liquid or gas solely on the basis of a comparison of the calculated critical temperature and the actual reservoir temperature.

Once the model of the fluid is defined, the following properties can be computed: surface tension between phases, viscosity of each phase, Condensate-Gas ratio (CGR) or Gas-Oil ratio (GOR), density of each phase, volumetric factors and compressibility, heat capacity, and saturation pressure (bubble or dew point). Thus, the EOS can be solved to obtain the saturation pressure at a given temperature. The density, gas-liquid ratios, and volumetric factors are byproducts of the EOS. Other properties such as heat capacity or viscosity are derived from the other properties in conjunction with information regarding the fluid composition.

When any of these properties is measured directly or indirectly by the MDT tool or any other logging technique, or is available from prior knowledge, it validates the EOS models as well as fits the EOS adjustable parameters. The latter is at the user's discretion but may be useful in estimating the uncertainty arising from the method used to calculate the phase envelope.

Furthermore, the properties measured and computed with this invention can be used in conjunction with other reservoir evaluation techniques for a compositional numerical simulation of the flow and production behavior of the reservoir.

Figure 4:
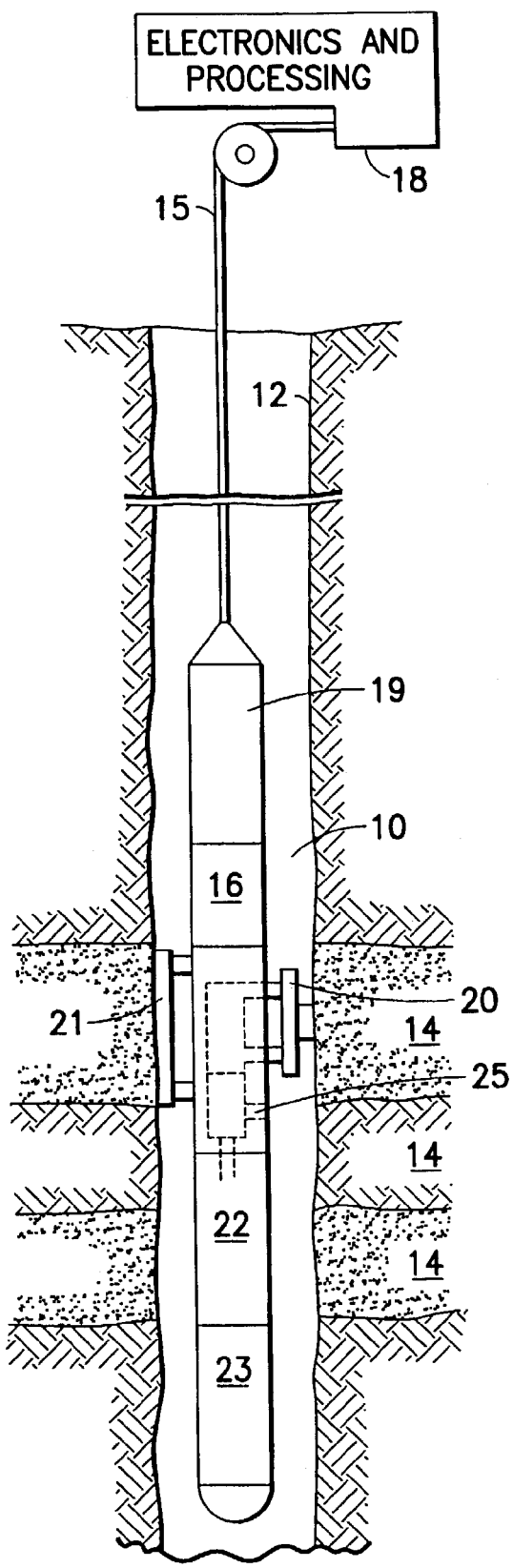
FIG. 4 is a diagram of an apparatus of the invention.

Turning now to FIG. 4, the preferred apparatus of the invention is seen. A borehole tool 10 is suspended in the borehole 12 from the lower end of a typical multiconductor cable 15 that is spooled in a usual fashion on a suitable winch (not shown) on the formation surface. The cable 15 is electrically coupled to an electrical control system 18 on the formation surface. The tool 10 includes an elongated body 19 which encloses the downhole portion of the tool control system 16. The elongated body 19 also carries a selectively extendable fluid admitting assembly 20 and a selectively extendable tool anchoring member 21 which are respectively arranged on opposite sides of the tool body. The fluid admitting assembly 20 is equipped for selectively sealing off or isolating selected portions of the wall of the borehole 12 such that pressure or fluid communication with the adjacent earth formation 14 is established. Also included with tool 10 are means for determining the downhole pressure and temperature (not shown) and a fluid analysis (optical) module 25 through which the obtained fluid flows. The fluid may thereafter be expelled through a port (not shown) or it may be sent to one or more fluid collecting chambers 22 and 23 which may receive and retain the fluids obtained from the formation. Control of the fluid admitting assembly, the fluid analysis section, and the flow path to the collecting chambers is maintained by the electrical control systems 16 and 18. As will be appreciated by those skilled in the art, the electrical control systems may include one or more (micro) processors, associated memory, and other hardware and/or software to implement the invention.

Using the apparatus of FIG. 4, a sample of formation fluid was obtained at a measured reservoir pressure (and temperature), and the information was processed with the CGA module/algorithm. The CGA module measures absorption spectra and translates them into concentrations of several molecular groups in the fluids of interest. In its present state the CGA module of the MDT tool provides measurements of the concentrations of methane ($CH_4$), a group containing ethane, propane, butane, and pentane fractions ($C_2H_6$, $C_3H_8$, i-$C_4H_{10}$, n-$C_4H_{10}$, i-$C_5H_{12}$, n-$C_5H_{12}$), a lump of hexane and heavier components ($C_6H_{14}+$), and carbon dioxide ($CO_2$), from which molar or weight fractions can be calculated. The (pseudo-) composition determined from the CGA is set forth in Table 2.

TABLE 2

|  | Mass Fraction (%) |
|---|---|
| CO2 | 3.5 |
| C1 | 41.1 |
| C2–5 | 22.0 |
| C6 | 33.4 |

Figure 5:
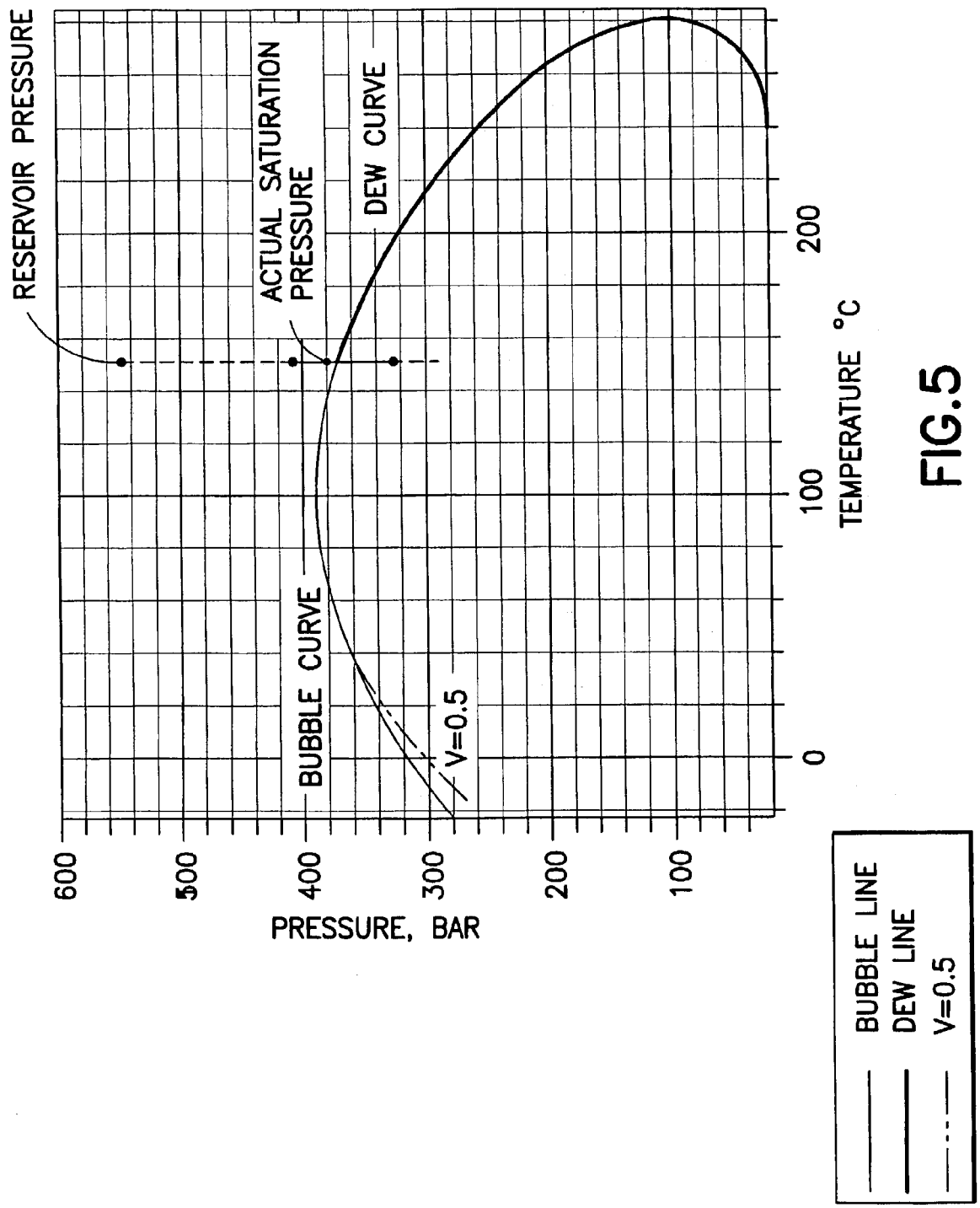
FIG. 5 is a pressure-temperature diagram for a pseudo-composition of hydrocarbons as determined by the CGA module of an MDT tool.

From this composition the phase diagram of FIG. 5 was obtained. The reservoir pressure and the actual saturation pressure measured in the laboratory are also plotted in FIG. 5. It can be observed from FIG. 5 that the type of fluid in the reservoir (which was measured to be at approximately 550 bar and 156° C.) is a retrograde condensate since that pressure/temperature combination is to the right side of the critical point and above the dew curve. As will be discussed hereinafter, this information is valuable since it dictates the considerations to be taken while sampling.

With the fluid characterized as above, the saturation pressure value calculated with the cubic EOS at 156° C. is 372 bar. Using a confidence interval of ±10% represented by the dark circles, the person in charge of the sampling would be advised not to lower the pressure below 410 bar.

For the particular fluid sampled by the apparatus of the invention, a laboratory compositional analysis was available and is shown in Table 3:

TABLE 3

| Component | Mole Fraction (%) |
|---|---|
| N2 | 0.51 |
| CO2 | 4.25 |
| C1 | 72.94 |
| C2 | 8.28 |
| C3 | 4.21 |
| iC4 | 0.70 |
| nC4 | 1.43 |
| iC5 | 0.51 |
| nC5 | 0.61 |
| C6 | 0.74 |
| C7 | 1.11 |
| C8 | 1.14 |
| C9 | 0.69 |
| C10 | 2.88 |

Figure 6:
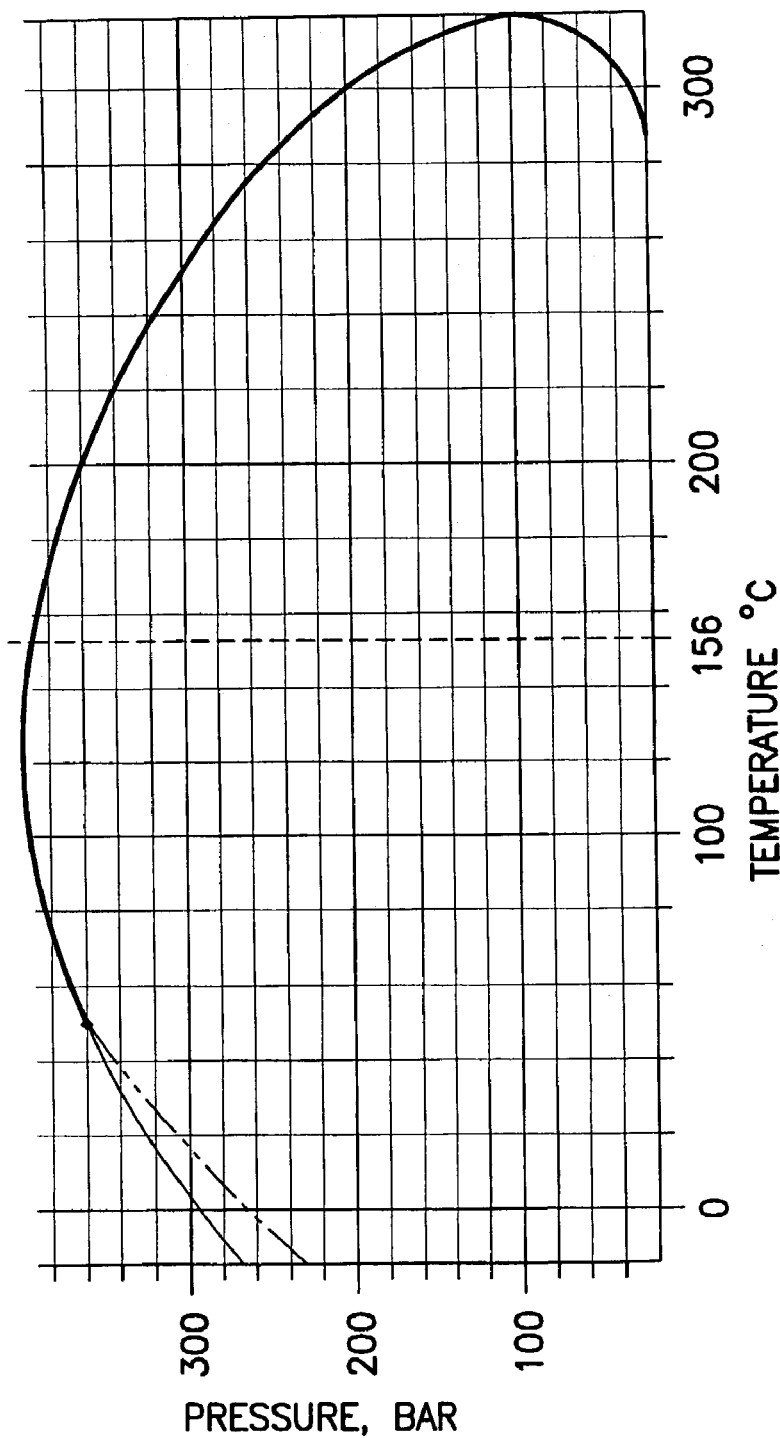
FIG. 6 is a pressure-temperature diagram for the actual composition of hydrocarbons utilized in generating FIG. 5.
Figure 7A:
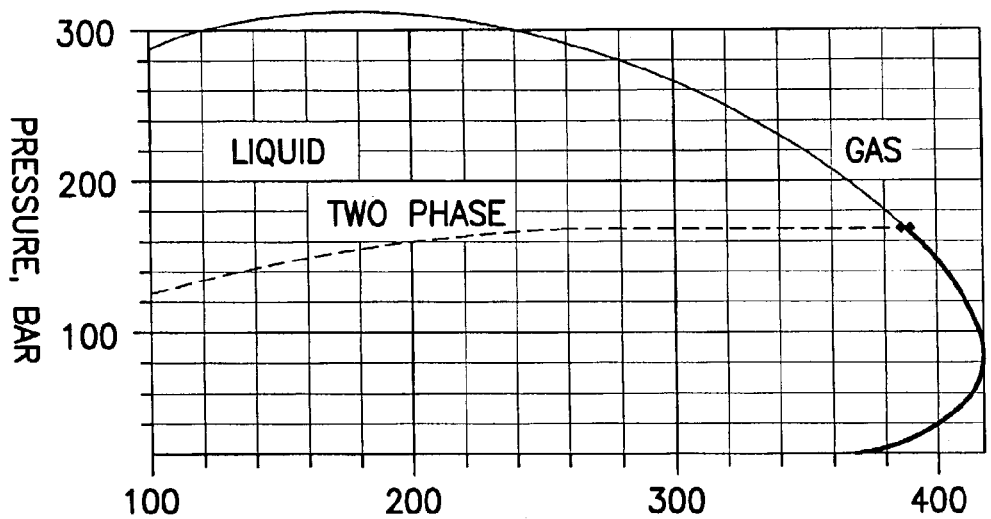
FIGS. 7a–7f are pressure-temperature diagrams for the actual composition of hydrocarbons utilized in generating FIG. 5 but with varying mole fractions of mud filtrate contaminating the sample.
Figure 7B:
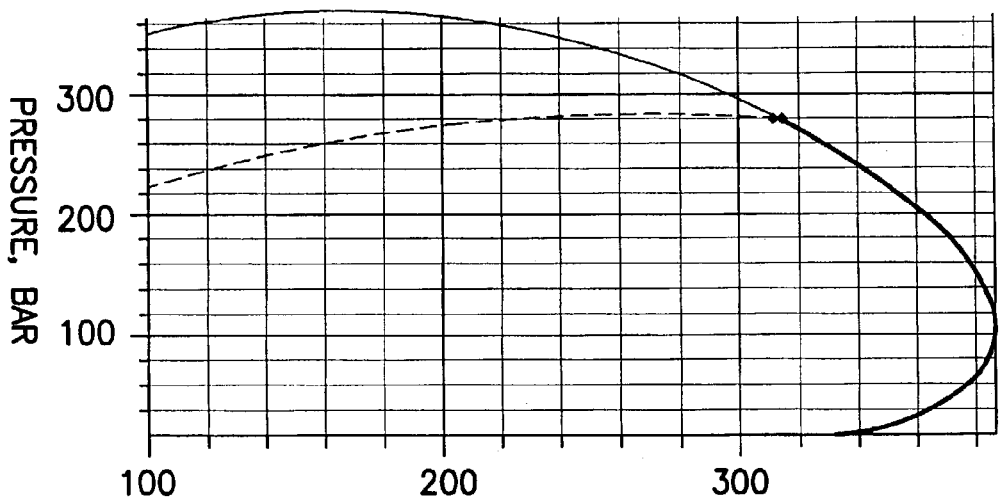
Figure 7C:
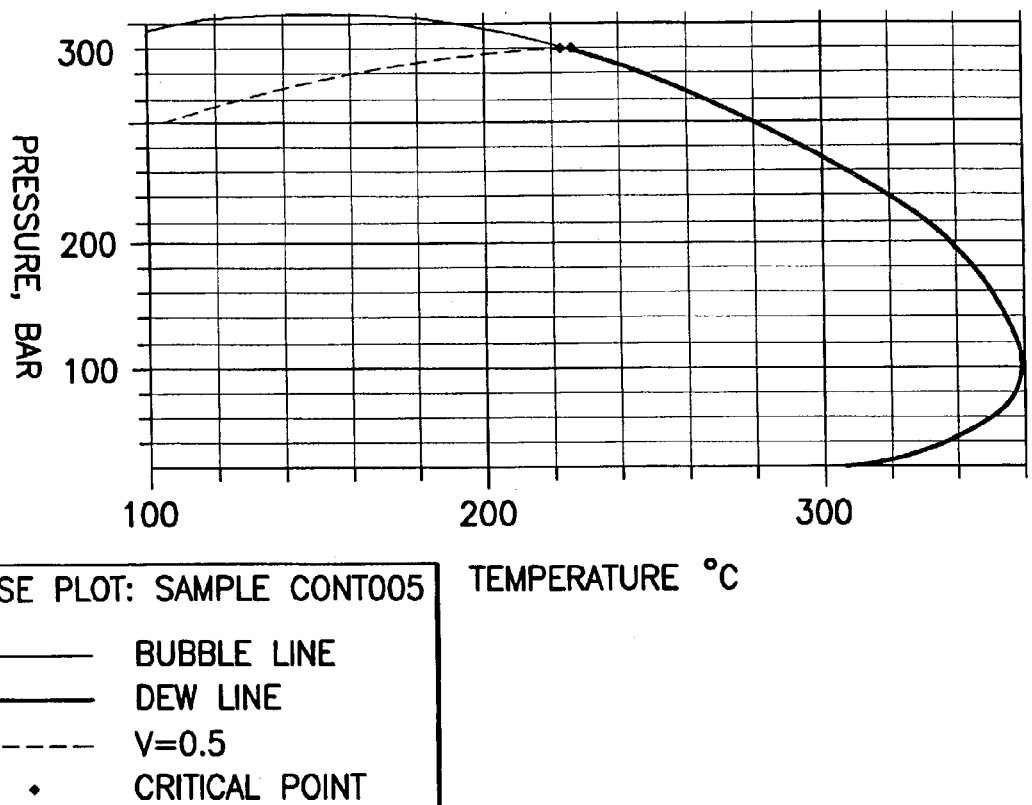
Figure 7D:
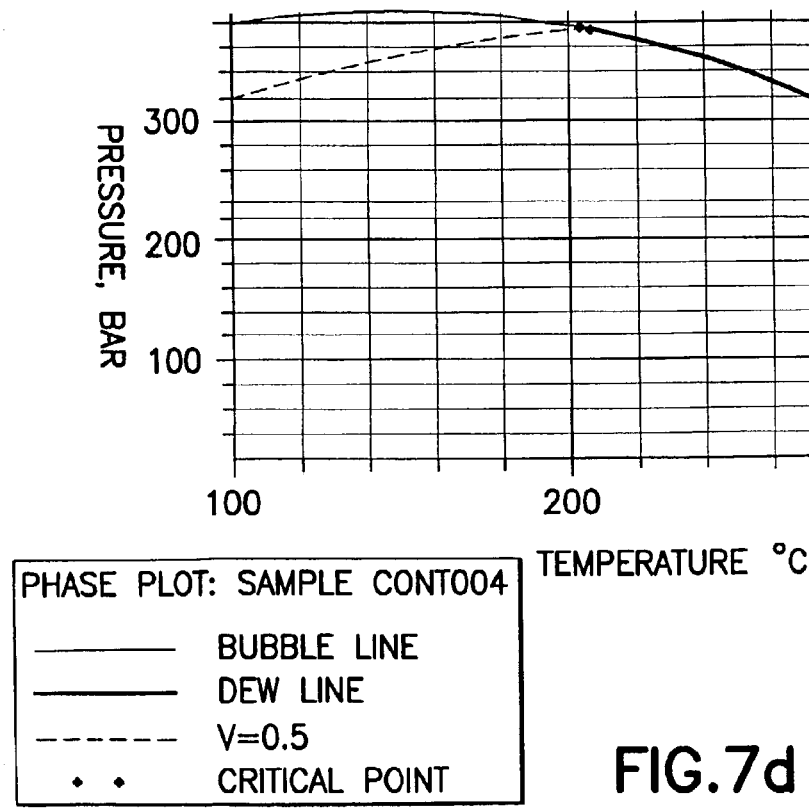
Figure 7E:
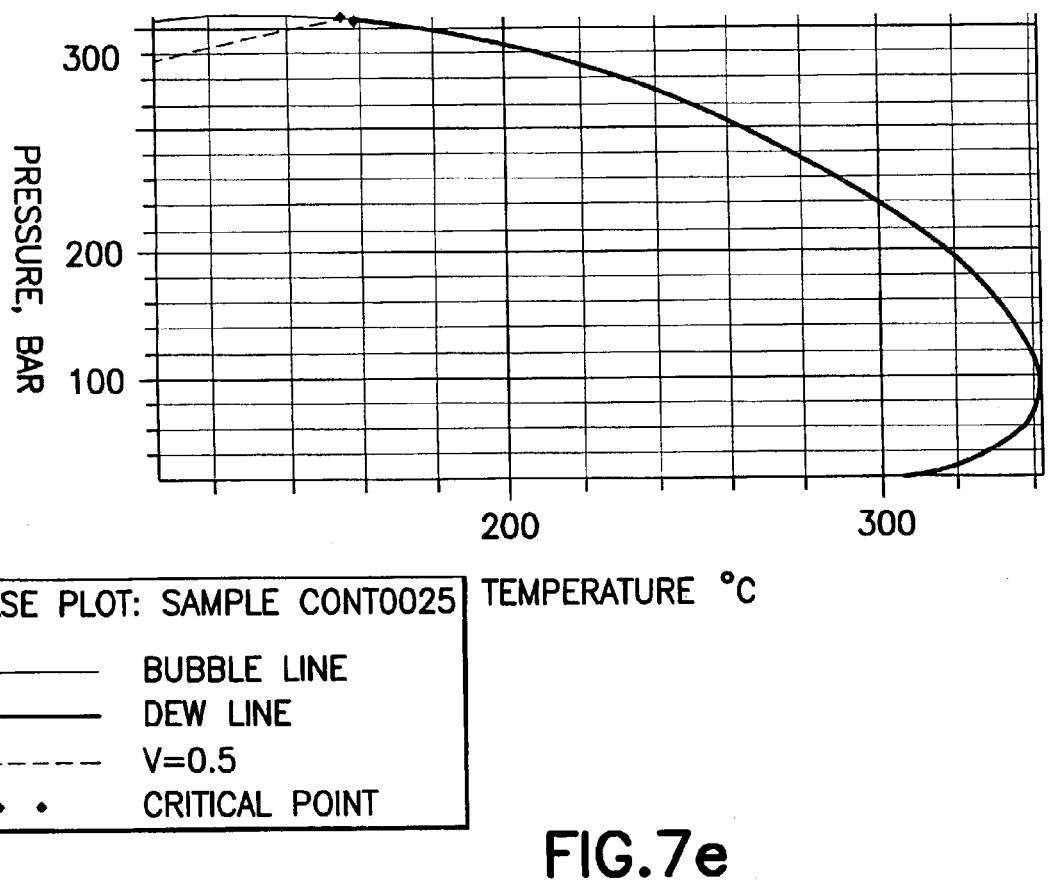
Figure 7F:
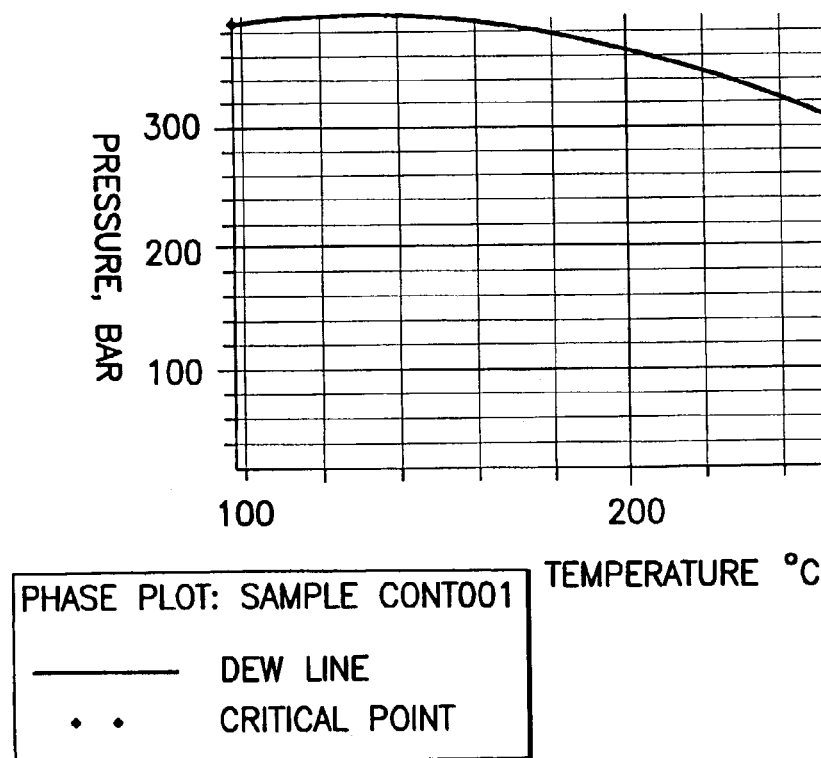

With the components of Table 3 as detailed, a phase diagram was generated and is shown in FIG. 6. As may seen from FIG. 6, at 156° C., the actual saturation pressure of the obtained fluid is 389.5 bar. This point is shown on the plot of FIG. 5 and falls within the confidence interval shown.

According to one aspect of the present invention, the generation of phase plots can be used to help determine the effect of borehole mud contamination on the obtained fluid sample. In particular, a tool such as shown in FIG. 4 is introduced into the borehole and stationed at a desired borehole depth which is typically selected based on an evaluation of the reservoir with open-hole logs in zones where it is expected to find a single-phase fluid (oil or gas). The tool probe enables hydraulic communication with the reservoir, and fluids are pumped out through the tool and analyzed in the optical module of the borehole tool. The first composition measurements are obtained, and usually correspond to a highly contaminated fluid from the near wellbore region where drilling fluid (e.g., an oil-based mud) filtrated into the reservoir and mixed with the native fluids (including, e.g., hydrocarbons). Quantitative estimates of contamination (i.e., the fraction of contamination) can be determined using algorithms which utilize near infrared optical analysis of samples obtained by the MDT such as disclosed in U.S. Pat. No. 6,350,986 to Mullins et al., and U.S. Pat. No. 6,274,865 to Schroer et al., both of which are hereby incorporated by reference herein in their entireties. The contamination estimate is equivalent to the mass fraction of contaminant in the oil-based-mud-filtrate/formation-fluid mixture.

The initial composition measurement of the contaminated sample is used to generate a phase diagram based on calculations performed with an equation of state. Knowing the fraction of contaminant in the mixture, the measured contaminated composition is inverted to obtain an estimate of the uncontaminated fluid. For example, if the compositional measurement determines the fraction of liquid in the sample along with some compositional analysis of gaseous components, then all of the contamination is assigned to the liquid composition, and the fraction of contamination may be subtracted from the liquid to give an estimate of the composition of the virgin fluid. The virgin fluid composition estimation can then be used to predict the phase diagram of the pure phase.

As fluids are pumped through the optical module of the MDT, the composition of the fluids is constantly being determined. Typically, as sampling progresses, progressively cleaner (less contaminated) samples are obtained. The phase diagrams can be generated continuously and the compositions inverted to estimate the uncontaminated sample based on the fraction of contaminant. These estimates should be in agreement with the initial estimate of the virgin fluid composition. By continuously finding estimated uncontaminated compositions and comparing to previous determinations, the contamination measurement can be validated.

The impact of contamination on various measurements and determinations made therefrom may be seen with reference to FIGS. 7a–7f. FIGS. 7a–7f show P-T diagrams for the sample set forth above in Table 3 but contaminated with different amounts of a mud filtrate composed of 50% nC16 and 50% nC18 (molar fractions). FIGS. 7a to 7e show the diagrams obtained for this mixture at different proportions (molar fractions) of the contaminant. For a 20% mole fraction of filtrate (FIG. 7a), the fluid at the (ambient) reservoir conditions of approximately 550 bar and approximately 156° C. is in the liquid phase, as the critical point for the contaminated mixture is at approximately 172 bar and approximately 390° C. As the contamination decreases from FIG. 7a to FIG. 7b (10% mole fraction of filtrate), FIG. 7c (5% mole fraction of filtrate), FIG. 7d (4% mole fraction of filtrate), and FIG. 7e (2.5% mole fraction of filtrate), the critical point moves towards a lower temperature (e.g., from approximately 390° C. to approximately 157° C.). With 2.5% mole fraction of filtrate, the critical point essentially coincides with the reservoir temperature. At this contamination level it could be erroneously concluded that the fluid in the reservoir is supercritical. At a 1% mole fraction of filtrate (FIG. 7f), the fluid is all in the gas phase at reservoir conditions (i.e., at 550 bar and 156° C.) and the dew pressure at the reservoir temperature is again 389 bar. Thus, it will be appreciated that if correction is not made for contamination, an incorrect determination can be made as to the state of the fluid in the formation.

Those skilled in the art will appreciate that when a large percentage of a formation fluid is constituted from longer carbon chains (e.g., C6+), the mud filtrate composed of 50% nC16 and 50% nC18 will have a smaller effect on the thermodynamic model of the fluid; and when a large percentage of the formation fluid is constituted from methane or short carbon chains, the typical oil-based mud filtrate will have a larger effect on the fluid model.

Figure 8:
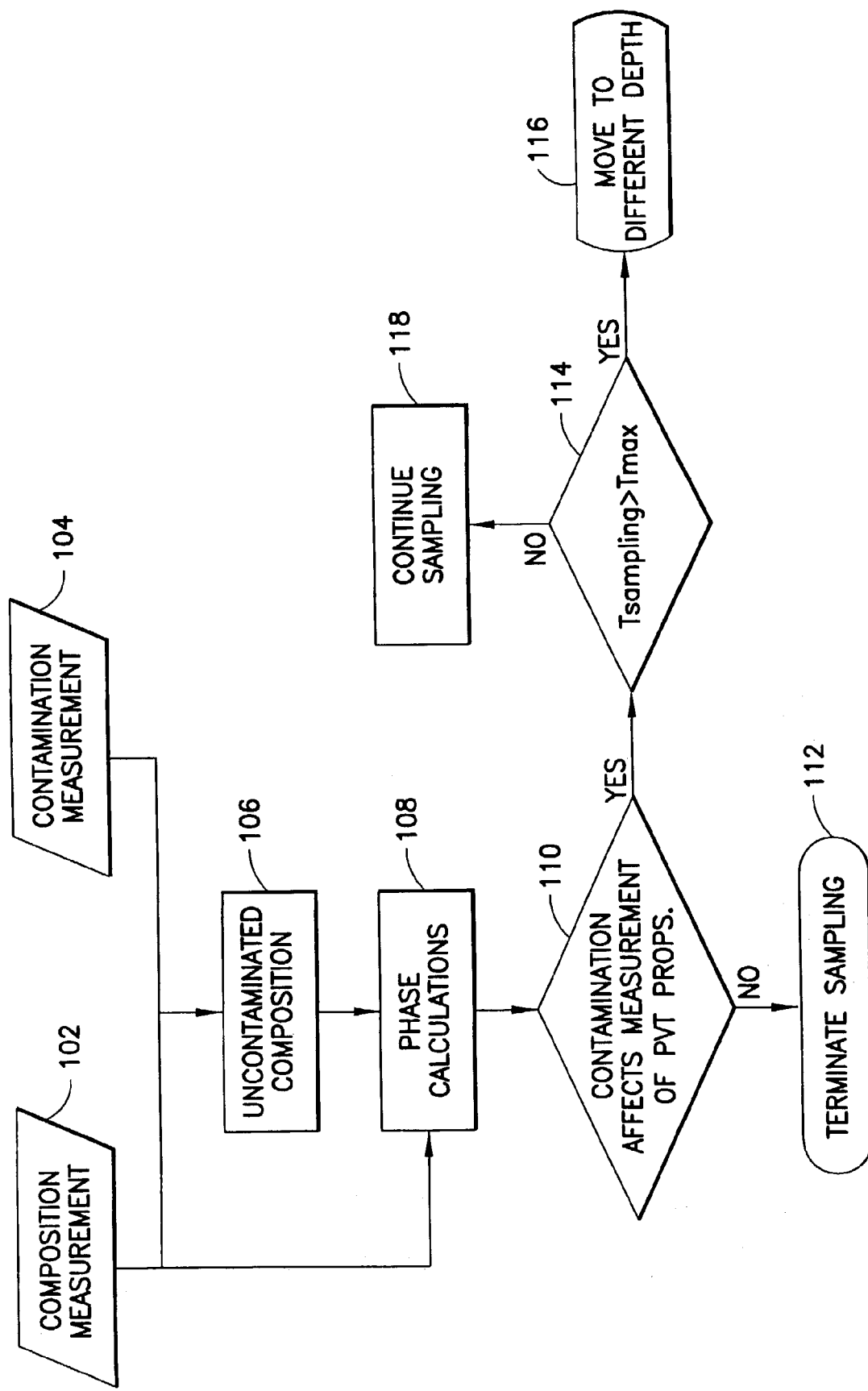
FIG. 8 is a flow chart illustrating the use of phase calculations in determining whether or not to continue sampling.

The provision of a downhole tool which can produce phase diagrams of in-situ fluids and which can account for mud filtrate contamination has numerous applications. For example, the characterization of the fluid sample with respect to its thermodynamic model can be used as a benchmark to determine the validity of the obtained sample, whether to retain the sample, and/or whether to obtain another sample at the location of interest. More particularly, and turning to FIG. 8, after a fluid sample is obtained by the borehole tool, a measurement of the composition or pseudo-composition of the (contaminated) sample is made at 102 and a measurement of the level of contamination is made at 104. With both measurements, and given knowledge of the constituents of the contaminants, determination of the constituents of the virgin (uncontaminated) fluid is found at 106. Utilizing equations of state, phase calculations of both the uncontaminated and the contaminated fluids may be made and compared at 108. The phase calculations may then be compared at 110 at the formation temperature and pressure, in order to determine whether the contamination significantly affects the PVT properties of the fluid. In other words, if the pressure and temperature of the formation are located on same portions of the P-T diagrams for the contaminated fluid and uncontaminated fluid indicating that the fluid is in the same phase in both cases, the contamination may not be considered "significant", and the sampling at that depth in the borehole may be completed at 112 with the storage (if desired) of the obtained sample. On the other hand, if the contamination significantly affects the PVT properties of the fluid, at 114, a determination is made as to whether the sampling time at the depth location in the formation has reached a maximum time. If so, at 116, the tool is preferably moved to a new location for sampling; while, if not, at 118, additional fluid samples may be obtained in the hope that fluid contamination will decrease to a level where it is not significant.

Continuous or multiple sampling, and the processing of data from the continuous or multiple sampling which results in multiple contamination measurements, multiple uncontaminated composition determinations, and multiple sets of phase calculations can be used in several manners. First, as multiple determinations are made of the contamination measurements and the uncontaminated composition, the certainty level with respect to these values increases. The certainty level can be provided along with the actual determination as a "product". Second, as will be discussed hereinafter with respect to FIGS. 10 and 11, in certain circumstances the initial phase calculations can be used to adjust the drawdown pressure in order to obtain a single phase fluid. Third, multiple determinations can be used to predict a contamination clean-up rate which in turn can be utilized in determining whether or not to continue sampling at the sampling location.

Figure 9:
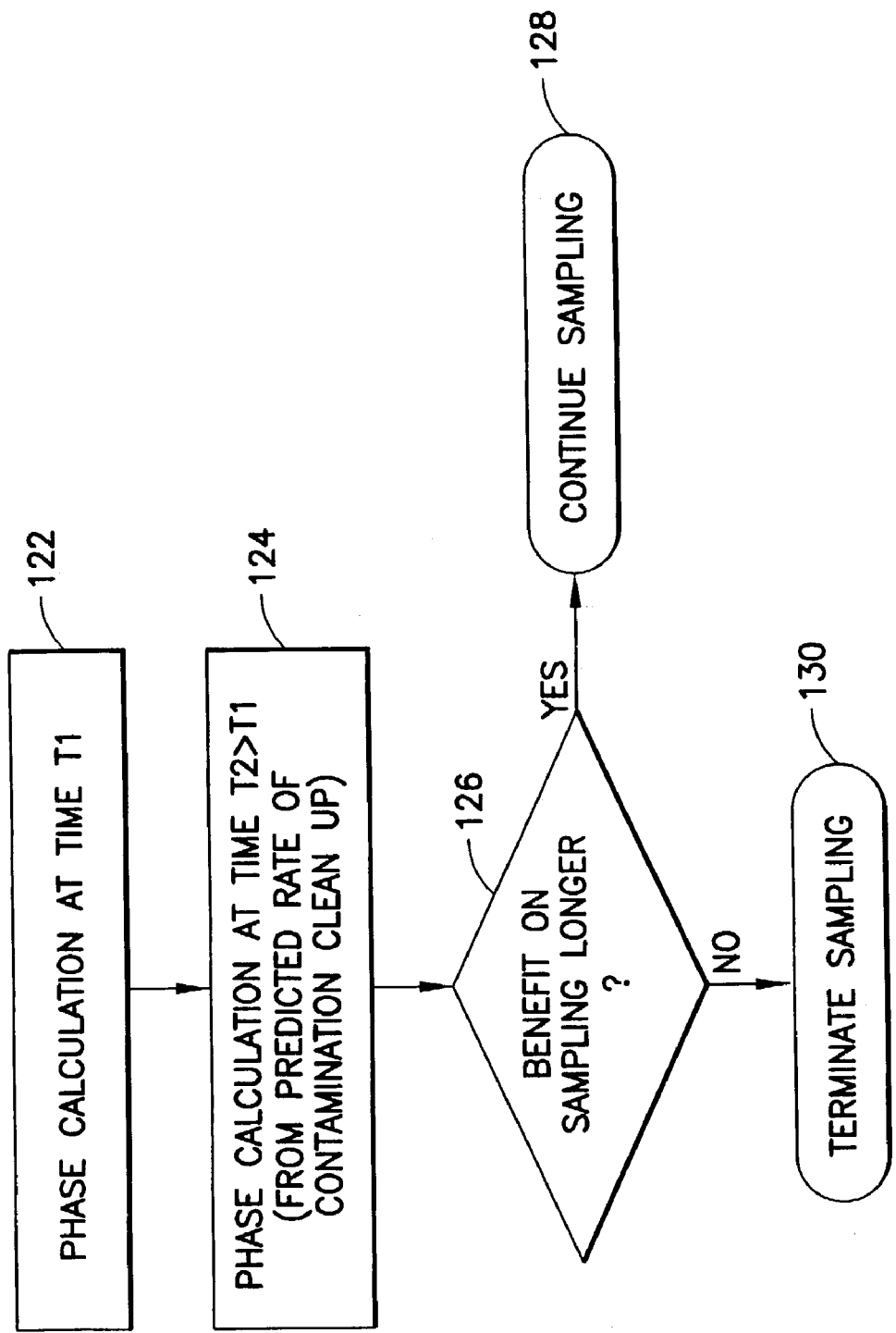
FIG. 9 is a flow chart illustrating the use of phase calculations made over time in a decision regarding whether or not to continue sampling.

Turning to FIG. 9, with a first phase calculation having been previously conducted at 122 on a first fluid sample, a second phase calculation is conducted at 124 on a second fluid sample. If desired, third and subsequent phase calculations (not shown) can be conducted on additional fluid samples. Based on the respective phase calculations, a determination is made as to the rate of contamination clean-up. If the rate of contamination clean-up suggests at 126 that an acceptable contamination level will be reached within a suitable timeframe, sampling continues at 128. If not, sampling is terminated at 130. It should be noted that the "acceptable contamination level" correlates to whether the level of contamination will significantly affect the PVT properties of the fluid as discussed above with reference to FIG. 8.

Figure 10:
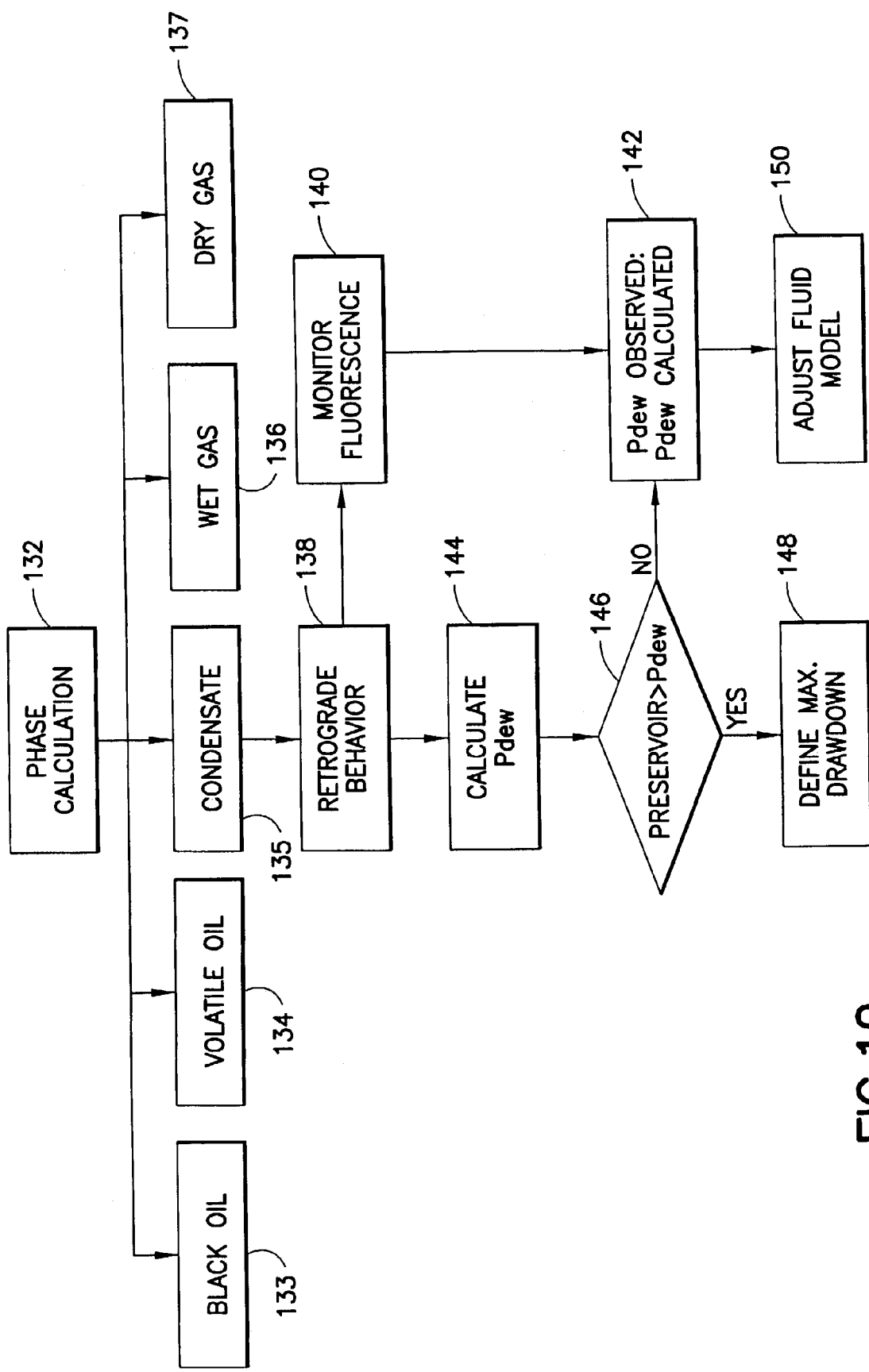
FIG. 10 is a flow chart illustrating the use of phase calculations in helping define drawdown pressures for retrograde condensates.

As previously suggested, the phase calculations of the invention can also be used to adjust drawdown (sampling) pressures. As seen in FIG. 10, based on the phase calculations at 132, and also with knowledge of the temperature and pressure of the formation, a determination can be made as to whether the in situ fluid is black oil 133, volatile oil 134, condensate 135, wet gas 136 or dry gas 137. In the case of condensate, if at 138 the fluid being sampled from the formation is a gas (i.e., the condensate is exhibiting "retrograde behavior"), as taught in co-owned concurrently filed U.S. application Ser. No. 10/309,850, entitled "Detecting Downhole Dew Precipitation in Oilfield Retrograde Condensate", which is hereby incorporated by reference herein in its entirety, the gas may be monitored for its fluorescence at 140, and its dew pressure observed at 142. Also, at 144, from the phase calculations, the dew pressure Pdew (i.e., the point on the dew curve corresponding to the in situ temperature) can be calculated. If at 146 the in situ pressure of the reservoir Preservoir is greater than the dew pressure, a maximum drawdown pressure drop (i.e., Preservoir-Pdew) is defined at 148 in order to maintain single phase flow into the borehole tool. This maximum drawdown pressure drop may be used in the sampling procedure to adjust the drawdown pressure utilized in obtaining samples. However, if the calculation of Preservoir from the phase calculations is not greater than Pdew, than retrograde behavior should not be observed. Thus, the Pdew calculated at 146 does not equate to the Pdew observed from the monitoring of fluorescence, and the fluid model should be accordingly adjusted at 150 by e.g., choosing different equations of state, adjusting parameters in the EOS, or adjusting the determination of the compositional components.

Figure 11:
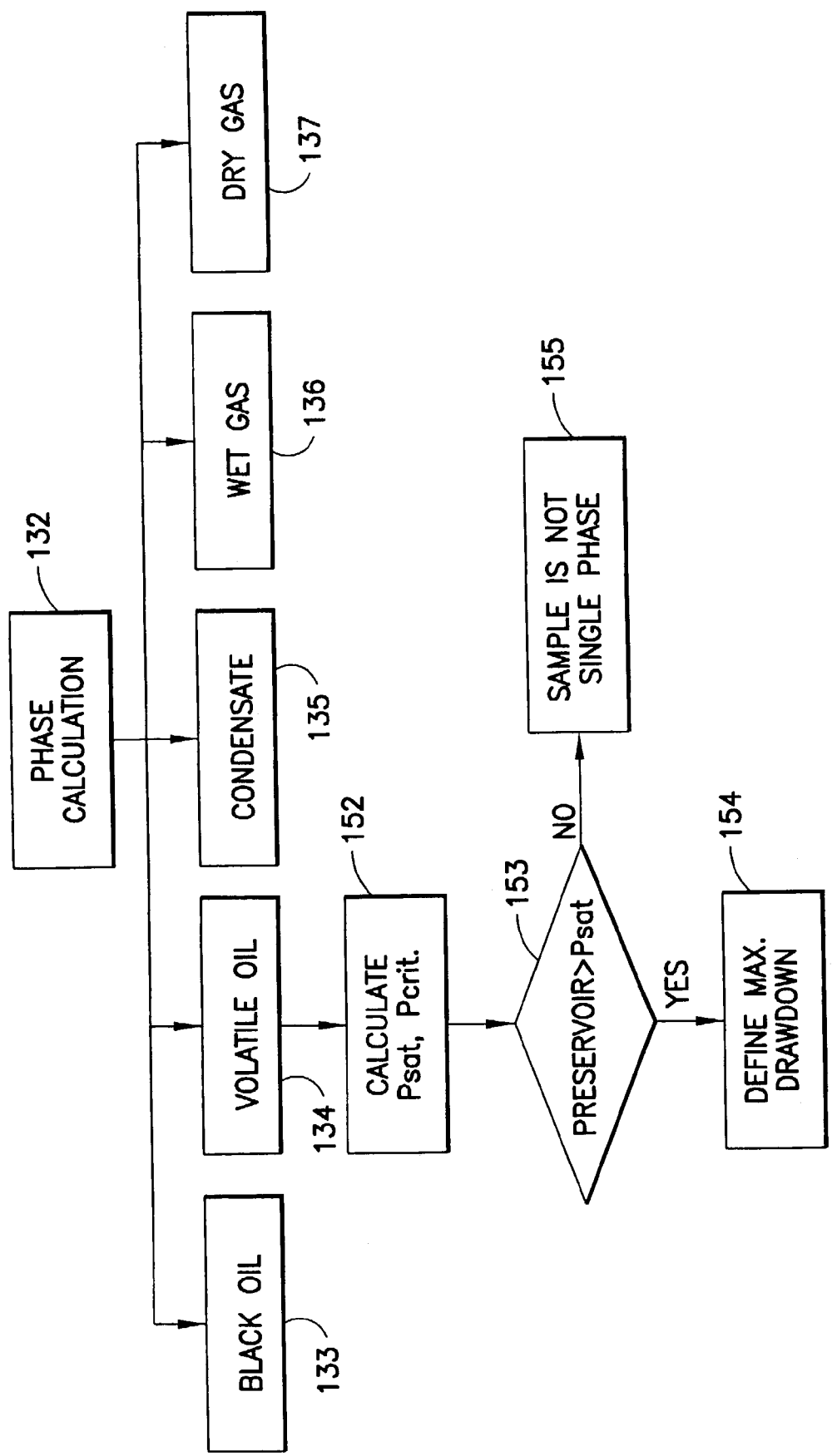
FIG. 11 is a flow chart illustrating the use of phase calculations in helping define drawdown pressures for volatile oils.

If the phase calculations at 132 suggest that the in situ fluid is volatile oil 134, as seen in FIG. 11, a different set of calculations may be conducted. With volatile oil, at 152 the saturation pressure Psat and optionally the critical pressure are calculated. If at 153 the reservoir pressure Preservoir is greater than Psat, a maximum drawdown pressure drop (i.e., Preservoir-Psat) is defined at 154 in order to maintain single phase flow (i.e., liquid) into the borehole tool. This maximum drawdown pressure drop may be used in the sampling procedure to adjust the drawdown pressure utilized in obtaining samples. In addition, if the drawdown pressure is to be adjusted, other adjustments (such as the contamination cleanup rate—FIG. 9) may be made to the system. However, if Preservoir is not greater than Psat, then the obtained sample should be a two phase sample 155. If desired, this determination can be compared to a determination of phase of the actual sample, and the fluid model accordingly adjusted if the prediction differs from the actual situation. It should be noted that the maximum drawdown pressure drop may also be used in making decisions regarding production of hydrocarbons from the formation.

According to another aspect of the invention, if it determined that the fluid sample was obtained near the bubble line of the sample, a decision may be made to find to conduct drawdown at different pressure drops in order to find an exact (actual) bubble point. The bubble point may then be used in making decisions regarding production of hydrocarbons from the formation.

It will be appreciated by those skilled in the art that one possible "output" of the apparatus of the invention is one or more P-T diagrams for each obtained sample with or without indications of certainty. In lieu of P-T diagrams, it is possible to provide for each depth of interest a numerical indication of the bubble or dew point at the temperature of the formation at that depth. Likewise, it is possible to simply provide an indication of a pressure under which two phase production would occur. Other possible outputs include, inter alia, density, gas-liquid ratio, and viscosity determinations, as well as evaluations of contamination effects on sample quality and fluid behavior.

The versatility of fluid composition measurements at different borehole depths opens the possibility of gaining a better understanding of the reservoir structure. Knowing the estimated compositional gradient, it is possible to compare the estimated composition at a different depth with the actual measurement at that depth to analyze variations. Abrupt changes in the composition that may or may not be accompanied by changes in the pressure gradient are an indication of vertical discontinuity in the reservoir structure.

Composition measurements along with real time phase calculation at different depths enables the computation and verification of important fluid properties such as saturation pressure, gas-liquid ratios, and liquid drop-out volumes on high quality single-phase samples obtained at downhole conditions without the risk of phase recombination on the formation surface. The variations of these properties with depth can be used as the basis for the construction of a fluid model for the whole reservoir.

A specific situation where fluid composition and phase behavior calculations are of great utility is tha analysis of reservoirs containing gas and liquid zones where it is of primary interest to identify if the gas is associated to the liquid. In this case the bubble point of the liquid hydrocarbon obtained from phase calculations and the compositional gradient give an indication of the communication between the two zones. Specifically, if the oil zone is not near its saturation pressure, then it is most likely not in communication with nearby gas zones. Conversely, if an oil is at its saturation pressure and a gas containing formation is nearby, it is likely that the two zones are in communication.

Another application is the case of thick reservoirs where compositional variations occur due to gravity and temperature gradients. Prediction of gas-oil fluid contacts in these cases is possible from the composition gradient. In reservoirs that span a large range of depths the composition variations can be tested following the previous procedure in selected wells.

There have been described and illustrated herein embodiments of methods and apparatus for characterizing formation fluids. While particular embodiments of the invention have been described, it is not intended that the invention be limited thereto, as it is intended that the invention be as broad in scope as the art will allow and that the specification be read likewise. Thus, while the invention was described with reference to generating P-T diagrams, it will be appreciated that the actual diagrams need not get generated, and that useful determinations can be made by finding specific points of interest such as the critical point and/or the bubble point or dew point for a particular in situ temperature. Further, while certain particular tools and modules such as the MDT and CGA were described as preferred, it will be appreciated that other tools capable of making determinations of fluid constituents may be utilized. Also, while the preferred embodiment of the invention utilizes optical analysis, those skilled in the art will appreciate that other compositional analysis mechanism, e.g., mass spectroscopy, gas chromatography, etc., may be employed. It will therefore be appreciated by those skilled in the art that yet other modifications could be made to the provided invention without deviating from its spirit and scope as claimed.

We claim:

1. A method of investigating a hydrocarbon bearing geological formation traversed by a borehole, comprising:
    a) acquiring a sample of fluid in the formation with a formation fluid sampling tool located in the borehole;
    b) conducting a compositional analysis of the fluid sample located in the sampling tool while said sampling tool is in the borehole, wherein said compositional analysis includes an identification of methane, and an identification of at least one additional hydrocarbon or group of hydrocarbons;
    c) relating the compositional analysis to a model of the thermodynamic behavior of the fluid; and
    d) based on said relating, predicting a phase behavior of fluid remaining in the formation, wherein
        said sample of fluid is a contaminated sample which is contaminated with drilling mud,
        said conducting a compositional analysis includes correcting for said drilling mud contamination in order to obtain an indication of an uncontaminated composition of fluids in the geological formation, and
        said relating the compositional analysis relates an uncontaminated composition to said model of said fluid.

2. A method according to claim 1, further comprising:
    e) determining whether said contamination significantly affects said predicting a phase behavior.

3. A method according to claim 2, further comprising:
    f) determining whether to terminate sampling based on a determination obtained at step e).

4. A method according to claim 1, further comprising:
    f) repeating steps a) and b) for a plurality of samples at a first location in the borehole;
    g) predicting a contamination clean-up rate based on step f); and
    h) determining whether to terminate sampling based on step g).

5. A method of investigating a hydrocarbon bearing geological formation traversed by a borehole, comprising:
    a) acquiring a sample of fluid in the formation with a formation fluid sampling tool located in the borehole;
    b) conducting a compositional analysis of the fluid sample located in the sampling tool while said sampling tool is in the borehole;
    c) relating the compositional analysis to a model of the thermodynamic behavior of the fluid; and
    d) based on said relating, predicting a phase behavior of fluid remaining in the formation wherein:
        said sample of fluid is a contaminated sample which is contaminated with drilling mud,
        said conducting a compositional analysis includes correcting for said drilling mud contamination in order to obtain an indication of an uncontaminated composition of fluids in the geological formation, and
        said relating the compositional analysis relates an uncontaminated composition to said model of said fluid.

6. A method according to claim 5, further comprising:
    e) determining whether said contamination significantly affects said predicting a phase behavior.

7. A method according to claim 6, further comprising:
    f) determining whether to terminate sampling based on a determination obtained at step e).

8. A method according to claim 5, further comprising:
    f) repeating steps a) and b) for a plurality of samples at a first location in the borehole;
    g) predicting a contamination clean-up rate based on step f); and
    h) determining whether to terminate sampling based on step g).

* * * * *